United States Patent [19]

Engel et al.

[11] 4,410,527

[45] Oct. 18, 1983

[54] SUBSTITUTED THIENOBENZODIAZEPINONES AND SALTS THEREOF

[75] Inventors: Wolfhard Engel; Günther Schmidt; Wolfgang Eberlein, all of Biberach; Günter Trummlitz, Warthausen, all of Fed. Rep. of Germany; Rudolf Hammer, Milan; Piero Del Soldato, Monza, both of Italy

[73] Assignee: Dr. Karl Thomae Gesellschaft mit beschränkter Haftung, Biberach an der Riss, Fed. Rep. of Germany

[21] Appl. No.: 462,182

[22] Filed: Jan. 31, 1983

[30] Foreign Application Priority Data

Feb. 6, 1982 [DE] Fed. Rep. of Germany ....... 3204169

[51] Int. Cl.³ .................... A61K 31/55; C07D 417/06
[52] U.S. Cl. .................. 424/250; 424/256; 424/267; 424/269; 260/239.3 T
[58] Field of Search ............... 260/239.3 T; 424/250, 424/256, 267, 269

[56] References Cited

FOREIGN PATENT DOCUMENTS 39519 11/1981 European Pat. Off. ....... 546/239.37

Primary Examiner—Robert T. Bond

Attorney, Agent, or Firm—Hammond & Littell, Weissenberger & Muserlian

[57] ABSTRACT

Compounds of the formula

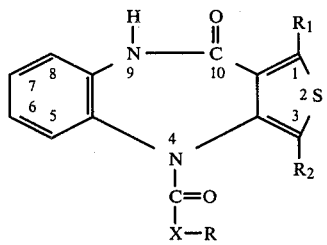

wherein
R is 1-methyl-4-piperididinyl, 4-methyl-1-piperazinyl, or 3 - or 3 -tropanyl, each of which may optionally have another methyl substituent attached to the heterocyclic ring;
$R_1$ is hydrogen or alkyl of 1 to 4 carbon atoms;
$R_2$ is hydrogen, halogen or alkyl of 1 to 4 carbon atoms; and
X is oxygen, —NH— or —N(CH$_3$)—;
and non-toxic, pharmacologically acceptable acid addition salts thereof. The compounds as well as their salts are useful as anti-ulcerogenics.

8 Claims, No Drawings

SUBSTITUTED THIENOBENZODIAZEPINONES AND SALTS THEREOF

This invention relates to novel substituted thienobenzodiazepinones and non-toxic acid addition salts thereof, to methods of preparing these compounds, to pharmaceutical compositions containing them as active ingredients, and to a method of using them as anti-ulcerogenics and gastric acid secretion inhibitors.

THE PRIOR ART

German Offenlegungsschrift No. 1,795,176 discloses certain dibenzodiazepinones having anti-ulcerogenic and secretion-inhibiting properties.

U.S. Pat. No. 3,953,430 discloses substituted dibenzodiazepines having antidepressant and analgesic properties.

U.S. Pat. No. 4,168,269 discloses substituted thienobenzodiazepinones which are useful as starting compounds for the preparation of thienobenzodiazpines having analgesic properties.

Published European Patent Application No. EP 0,039,519 discloses thienobenzodiazepinones having antiulcerogenic and secretion-inhibiting properties.

OBJECTS OF THE INVENTION

It is an object of the present invention to provide novel aminoacyl-substituted thienobenzodiazepinones having useful pharmacodynamic properties superior to those of the related compounds disclosed in the prior art.

Other objects and advantages of the invention will become apparent as the description thereof proceeds.

DESCRIPTION OF THE INVENTION

More particularly, the present invention relates to a novel class of aminoacyl-substituted thienobenzodiazepinones represented by the formula

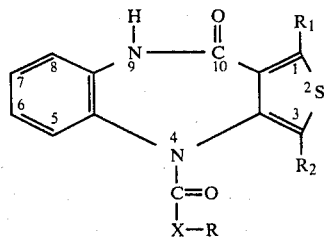

(I)

wherein
R is 1-methyl-4-piperidinyl, 4-methyl-1-piperazinyl, or 3α- or 3β-tropanyl, each of which may optionally have another methyl substituent attached to the heterocyclic ring;
$R_1$ is hydrogen or alkyl of 1 to 4 carbon atoms;
$R_2$ is hydrogen, halogen or alkyl of 1 to 4 carbon atoms; and
X is oxygen, —NH— or —N(CH$_3$)—; and non-toxic, pharmacologically acceptable acid addition salts thereof.

Examples of alkyl of 1 to 4 carbon atoms are methyl, ethyl, propyl, isopropyl, n-butyl, isobutyl, sec. butyl and tert. butyl, methyl being preferred.

Examples of halogen are bromine and especially chlorine.

Thus, a preferred subgenus is constituted by those compounds of the formula I
wherein
R is 1-methyl-4-piperidinyl, 4-methyl-1-piperazinyl, or endo- or exo-8-methyl-8-azabicyclo[3,2,1]oct-3-yl (i.e. 3α- or 3β-tropanyl);
$R_1$ is hydrogen or methyl;
$R_2$ is chlorine, hydrogen or methyl; and
X is oxygen, —NH— or —N(CH$_3$)—;
and non-toxic, pharmacologically acceptable acid addition salts thereof.

Specific examples of compounds of the formula I are the following:

4,9-Dihydro-4-{[(1-methyl-4-piperidinyl)oxy]carbonyl}-10H-thieno[3,4-b][1,5]benzodiazepin-10-one, cis-4,9-Dihydro-4-{[(1,2-dimethyl-4-piperidinyl)oxy]carbonyl}-10H-thieno[3,4-b][1,5]benzodiazepin-10-one, trans-4,9-Dihydro-4-{[(1,2-dimethyl-4-piperidinyl)oxy]carbonyl}-10H-thieno[3,4-b][1,5]benzodiazepin-10-one, cis-4,9-Dihydro-4-{[(1,3-dimethyl-4-piperidinyl)oxy]carbonyl}-10H-thieno[3,4-b][1,5]benzodiazepin-10-one, trans-4,9-Dihydro-4-{[(1,3-dimethyl-4-piperdinyl)oxy]carbonyl}-10H-thieno[3,4-b][1,5]benzodiazepin-10-one, 4,9-Dihydro-4-{[(1-methyl-4-piperidinyl)amino]carbonyl}-10H-thieno[3,4-b][1,5]benzodiazepin-10-one, cis-4,9-Dihydro-4-{[(1,2-dimethyl-4-piperidinyl)amino]carbonyl}-10H-thieno[3,4-b][1,5]benzodiazepin-10-one, trans-4,9-Dihydro-4-{[(1,2-dimethyl-4-piperidinyl)amino]carbonyl}-10H-thieno[3,4-b][1,5]benzodiazepin-10-one, cis-4,9-Dihydro-4-{[(1,3-dimethyl-4-piperidinyl)amino]carbonyl}-10H-thieno[3,4-b][1,5]benzodiazepin-10-one, trans-4,9-Dihydro-4-{[(1,3-dimethyl-4-piperidinyl)amino]carbonyl}-10H-thieno[3,4-b][1,5]benzodiazepin-10-one, 4,9-Dihydro-1-methyl-4-{[(1-methyl-4-piperidinyl)oxy]carbonyl}-10H-thieno[3,4-b][1,5]benzodiazepin-10-one, 4,9-Dihydro-3-methyl-4-{[(1-methyl-4-piperidinyl)oxy]carbonyl}-10H-thieno[3,4-b][1,5]-benzodiazepin-10-one, 4,9-Dihydro-1,3-dimethyl-4-{[(1-methyl-4-piperidinyl)oxy]carbonyl}-10H-thieno[3,4-b][1,5]benzodiazepin-10-one, 3-Chloro-4,9-dihydro-4-{[(1-methyl-4-piperidinyl)oxy]carbonyl}-10H-thieno[3,4-b][1,5]benzodiazepin-10-one, 4,9-Dihydro-1-methyl-4-{[(1-methyl-4-piperidinyl)amino]carbonyl}-10H-thieno[3,4-b][1,5]benzodiazepin-10-one, 4,9-Dihydro-3-methyl-4-{[(1-methyl-4-piperidinyl)amino]carbonyl}-10H-thieno[3,4-b][1,5]benzodiazepin-10-one, 4,9-Dihydro-1,3-dimethyl-4-{[(1-methyl-4-piperidinyl)amino]carbonyl}-10H-thieno[3,4-b][1,5]benzodiazepin-10-one, 3-Chloro-4,9-dihydro-4-{[(1-methyl-4-piperidinyl)amino]carbonyl}-10H-thieno[2,4-b][1,5]benzodiazepin-10-one, 4,9-Dihydro-4-{[(4-methyl-1-piperazinyl)amino]carbonyl}-10H-thieno[3,4-b][1,5]benzodiazepin-10-one, 4,9-Dihydro-4-{[(3,4-dimethyl-1-piperazinyl)amino]-carbonyl}-10H-thieno[3,4-b][1,5]benzodiazepin-10-one, 4,9-Dihydro-4-{[(2,4-dimethyl-1-piperazinyl)amino]-carbonyl}-10H-thieno[3,4-b][1,5]benzodiazepin-10-one, 4,9-Dihydro-4-{[(4-methyl-1-piperazinyl)oxy]carbonyl}-10H-thieno[3,4-b][1,5]benzodiazepin-10-one, 4,9-Dihydro-4-{[(3,4-dimethyl-1-piperazinyl)oxy]carbonyl}-10H-thieno[3,4-b][1,5]benzodiazepin-10-one, 4,9-Dihydro-4-{[(2,4-dimethyl-1-piperazinyl)oxy]carbonyl}-10H-thieno[3,4-b][1,5-benzodiazepin-10-one, 4,9-Dihydro-1-methyl-4-{[(4-methyl-1-piperazinyl)amino]carbonyl}-10H-thieno[3,4-b][1,5]benzodiazepin-10-one, 4,9-Dihydro-3-methyl-4-{[(4-methyl-1-piperazinyl)amino]carbonyl}-10H-thieno[3,4-b][1,5]benzodiazepin-10-one, 4,9-Dihydro-1,3-dimethyl-4-{[(4-methyl-1-piperazinyl)amino]carbonyl}-10H-thieno[3,4-b][1,5]benzodiazepin-10-one, 3-Chloro-4,9-dihydro-4-{[(4-methyl-1-piperazinyl)amino]carbonyl}-10H-thieno[3,4-b][1,5]benzodiazepin-10-one, 4,9-Dihydro-1-methyl-4-{[(4-methyl-1-piperazinyl)oxy]carbonyl}-10H-thieno[3,4-b][1,5]benzodiazepin-10-one, 4,9-Dihydro-3-methyl-4-{[(4-methyl-1-piperazinyl)oxy]carbonyl}-10H-thieno[3,4-b][1,5]benzodiazepin-10-one, 4,9-Dihydro-1,3-dimethyl-4-{[(4-methyl-1-piperazinyl)oxy]carbonyl}-10H-thieno[3,4-b][1,5]benzodiazepin-10-one, 3-Chloro-4,9-dihydro-4-{[(4-methyl-1-piperazinyl)oxy]carbonyl}-10H-thieno[3,4-b][1,5]benzodiazepin-10-one, endo-4,9-Dihydro-4-{[(8-methyl-8-azabicyclo[3,2,1]oct-3-yl)oxy]carbonyl}-10H-thieno[3,4-b][1,5]benzodiazepin-10-one, exo-4,9-Dihydro-4-{[(8-methyl-8-azabicyclo[3,2,1]oct-3-yl)oxy]carbonyl}-10H-thieno[3,4-b][1,5]-benzodiazepin-10-one, endo-4,9-Dihydro-4-{[(8-methyl-8-azabicyclo[3,2,1]oct-3-yl)amino]carbonyl}-10H-thieno[3,4-b][1,5]benzodiazepin-10-one, exo-4,9-Dihydro-4-{[(8-methyl-8-azabicyclo[3,2,1]oct-3-yl)-amino]carbonyl}-10H-thieno[3,4-b][1,5]benzodiazepin-10-one, endo-4,9-Dihydro-1-methyl-4-{[(8-methyl-8-azabicyclo[3,2,1]oct-3-yl)oxy]carbonyl}-10H-thieno[3,4-b][1,5]benzodiazepin-10-one, endo-4,9-Dihydro-3-methyl-4-{[(8-methyl-8-azabicyclo[3,2,1]oct-3-yl)oxy]carbonyl}-10H-thieno[3,4-b][1,5]benzodiazepin-10-one, endo-4,9-Dihydro-1,3-dimethyl-4-{[(8-methyl-8-azabicyclo[3,2,1]oct-3-yl)oxy]carbonyl}-10H-thieno[3,4-b][1,5]benzodiazepin-10-one, endo-3-Chloro-4,9-dihydro-4-{[(8-methyl-8-azabicyclo[3,2,1]oct-3-yl)oxy]carbonyl}-10H-thieno[3,4-b][1,5]benzodiazepin-10-one, endo-4,9-Dihydro-1-methyl-4-{[(8-methyl-8-azabicyclo[3,2,1]oct-3-yl)amino]carbonyl}-10H-thieno[3,4-b][1,5]benzodiazepin-10-one, endo-4,9-Dihydro-3-methyl-4-{[(8-methyl-8-azabicyclo[3,2,1]oct-3-yl)amino]carbonyl}-10H-thieno[3,4-b][1,5]benzodiazepin-10-one, endo-4,9-Dihydro-1,3-dimethyl-4-{[(8-methyl-8-azabicyclo[3,2,1]oct-3-yl)amino]carbonyl}-10H-thieno[3,4-b][1,5]benzodiazepin-10-one, endo-3-Chloro-4,9-dihydro-4-{[(8-methyl-8-azabicyclo[3,2,1]oct-3-yl)amino]carbonyl}-10H-thieno[3,4-b][1,5]benzodiazepin-10-one, exo-4,9-Dihydro-3-methyl-4-{[(8-methyl-8-azabicyclo[3,2,1]oct-3-yl)amino) carbonyl}-10H-thieno[3,4-b][1,5]benzodiazepin-10-one, 4,9-Dihydro-4-{[N-methyl-N-(1-methyl-4-piperidinyl)amino]carbonyl}-10H-thieno[3,4-b][1,5]benzodiazepin-10-one, 4,9-Dihydro-1-methyl-4-{[N-methyl-N-(1-methyl-4-piperidinyl)amino]carbonyl}-10H-thieno[3,4-b][1,5]benzodiazepin-10-one, 4,9-Dihydro-3-methyl-4-{[N-methyl-N-(1-methyl-4-piperidinyl)amino]carbonyl}-10H-thieno[3,4-b][1,5]benzodiazepin-10-one, 4,9-Dihydro-1,3-dimethyl-4-{[N-methyl-N-(1-methyl-4-piperidinyl)amino]carbonyl}-10H-thieno[3,4-b][1,5]benzodiazepin-10-one, and 3-Chloro-4,9-dihydro-4-{[N-methyl-N-(1-methyl-4-piperidinyl)amino]carbonyl}-10H-thieno[3,4-b][1,5]benzodiazepin-10-one.

The present invention further relates to novel acyl-substituted thienobenzodiazepinones of the formula

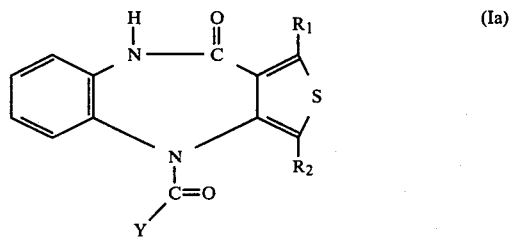

wherein $R_1$ and $R_2$ have the same meanings as in formula I;

Y is halogen, preferably bromine or chlorine, or —$OR_3$; and $R_3$ is unsubstituted or halo-substituted alkyl of 1 to 5 carbon atoms, phenyl, halo-substituted phenyl, nitro-substituted phenyl, or aralkyl of 7 to 15 carbon atoms; which are useful as intermediates for the preparation of compounds of the formula I.

Examples of $R_3$ are methyl, ethyl, n-butyl, isobutyl, benzyl, 9-fluorenyl-methyl, phenyl, 4-nitrophenyl, 2,2,2-trichloroethyl, 2,4,5-trichlorophenyl and 2,2,2-trichlorotert. butyl.

The compounds of the formula I may be prepared by the following methods:

Method A

By reacting a thienobenzodiazepinone of the formula Ia with a compound of the formula

H—X—R  (II)

wherein X and R have the meanings previously defined.

The reaction may be carried out in the absence or preferably in the presence of an inert solvent, for example water, toluene or alcohols such as methanol, ethanol or isopropanol, but preferably in the presence of an aprotic polar solvent, such as tetrahydrofuran, 1,4-dioxane, acetonitrile, N,N-dimethylformamide, dimethylsulfoxide, hexamethylphosphoric acid triamide or mixtures thereof, and at temperatures between 0° C. and the boiling point of the solvent in question, preferably between 40° and 100° C. It has proved helpful to use additionally an inorganic or organic base, for example alkali metal or alkaline earth metal hydroxides, alkoxides or carbonates, such as sodium hydroxide, sodium methoxide, potassium tert. butoxide, sodium carbonate or potassium carbonate; or tertiary amines, such as triethylamine, ethyl diisopropylamine, N,N-dimethylaniline or pyridine; and to perform the reaction in the presence of an excess of a compound of the formula II.

Method B

By reacting a thienobenzodiazepinone of the formula Ia with a metal compound of the formula $$M-X-R \qquad (IIa)$$

wherein

X and R have the meanings previously defined, and

M is an alkali metal atom or one equivalent of an alkaline earth metal atom.

A compound of the formula IIa can readily be prepared in situ from a compound of the formula II by reacting it with an alkali metal or alkaline earth metal, for example with sodium, potassium or barium, or with an alkali metal or alkaline earth metal hydride, for example with sodium, potassium or calcium hydride, or by reacting it with an alkali or alkaline earth organometallic compound, for example with n-butyl lithium or phenyl lithium.

Method C

By reacting a thienobenzodiazepinone of the formula

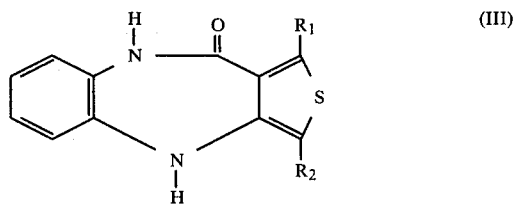

wherein $R_1$ and $R_2$ have the meanings previously defined, with a chlorocarbonic acid derivative of the formula

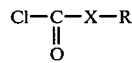

or with an isocyanate of the formula $$O=C=N-R \qquad (Va)$$

wherein X and R have the meanings previously defined. The reaction is carried out in an inert organic solvent, for example in an aromatic hydrocarbon such as toluene, chlorobenzene or xylene; in an ether such as diisopropyl ether, tetrahydrofuran or dioxane; in an acyclic or cyclic aliphatic ketone such as pentan-3-one; in a chlorinated aliphatic hydrocarbon such as 1,2-dichloroethane; or in other solvents such as acetonitrile or dimethylformamide, or in mixtures thereof, optionally in the presence of a tertiary organic base such as pyridine, and at temperatures up to the boiling point of the reaction mixture.

A base of the formula I thus obtained can subsequently be converted into a non-toxic, pharmacologically acceptable acid addition salt thereof, or any such acid addition salt obtained may be converted into the free base or another non-toxic, pharmacologically acceptable acid addition salt.

Examples of non-toxic, pharmacologically acceptable acid addition salts are those formed with hydrochloric acid, hydrobromic acid, sulfuric acid, methylsulfuric acid, phosphoric acid, tartaric acid, fumaric acid, citric acid, maleic acid, succinic acid, gluconic acid, malic acid, p-toluenesulfonic acid, methanesulfonic acid or amidosulfonic acid.

An acid addition salt is obtained by dissolving the free base in a suitable solvent, for example in water, acetone, an alkanol such as ethanol or isopropanol, or an acyclic or cyclic ether such as diethyl ether or tetrahydrofuran, which contains the desired acid or to which the desired acid is subsequently added. The salt is recovered by filtering, precipitating with a medium in which the acid addition salt is not soluble, or by evaporating the solvent. The salt may also be converted into another salt, for example a pharmacologically acceptable acid addition salt, by converting it into the base and reacting the base with another acid.

Some of the thienobenzodiazepinones of the formula I contain one or more asymmetric carbon atoms in the side chain —CO—X—R. These compounds may therefore occur in two diasteroisomeric cis- and trans-forms or as the enantiomeric (+) and (−) forms. The invention includes the individual isomers and the mixtures thereof.

The diasteroisomers may be separated on the basis of their different physico-chemical properties, for instance by fractional recrystallization from a suitable solvent.

Racemates of the compounds of the formula I may be separated according to known methods, for example by using an optionally active acid such as (+)- or (−)-tartaric acid, or a derivative thereof such as (+)- or (−)-diacetyl tartaric acid, (+)- or (−)-monomethyl tartrate or (+)-camphorsulfonic acid.

In a conventional method for separating isomers, the racemate of a compound of the formula I is reacted with an equimolar quantity of one of the above-mentioned optically active acids in a solvent, and the crystalline optically active salts obtained are separated on the basis of their different solubilities. This reaction may be carried out in any type of solvent, provided that the salts have sufficiently different solubilities in the solvent. Preferably, methanol, ethanol or a mixture thereof, for example in proportions of 50:50 by volume, is used. Then, each of the optically active salts is dissolved in water, the solution is neutralized with a base such as sodium carbonate or potassium carbonate, and in this way the corresponding free base is obtained in the (+) or (−) form.

The intermediate compounds of the formula Ia are obtained by reacting a thienobenzodiazepinone of the formula

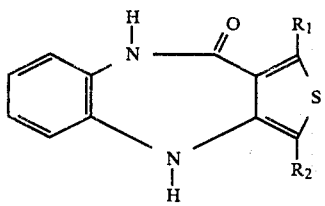 (III)

wherein

R₁ and R₂ have the meanings previously defined, with a halocarbonic acid derivative of the formula

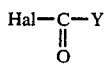 (IV)

wherein Hal is bromine or, preferably, chlorine, and Y has the meanings previously defined. The reaction is carried out in an inert organic solvent, such as aromatic hydrocarbons, for example toluene, chlorobenzene or xylene; acyclic or cyclic ethers such as diisopropyl ether, tetrahydrofuran or dioxane; acyclic or cyclic aliphatic ketones such as pentan-3-one; chlorinated aliphatic hydrocarbons, such as 1,2-dichloro-ethane; or other solvents such as acetonitrile or dimethylformamide, or mixtures thereof, in the presence of a tertiary organic base, preferably pyridine, and at temperatures up to, at most, the boiling point of the solvent or mixture of solvents, preferably between +30° and +100° C.

The starting compounds of the formula II are known or may be prepared in analogy to processes described in the literature. For example, 1-hydroxy-4-methyl-piperazine is obtained as described by S. M. Riba, A. S. Issa and Y. A. Beltagy, Pharmazie 33, 711 (1978), by reacting bis[N-(2-chloroethyl)]-methylamine with hydroxylamine hydrochloride in aqueous ethanolic solution and in the presence of potassium carbonate.

The starting compounds of the formula III are prepared according to U.S. Pat. No. 3,953,430 by reacting o-phenylenediamine with a tetrahydrothiophene carboxylic acid derivative of the formula

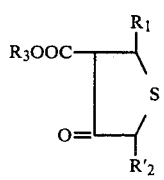 (VI)

wherein R₁ has the meanings previously defined, R₂' is hydrogen or alkyl of 1 to 4 carbon atoms, and R₃ is hydrogen or alkyl of 1 to 5 carbon atoms. The reaction is effected, for example, in an inert solvent such as toluene at temperatures up to the boiling point of the reaction mixture. A tetrahydrothienobenzodiazepinone of the formula

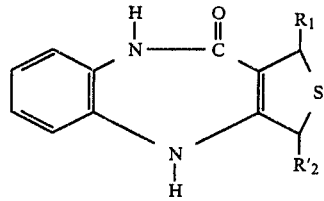 (VII)

is thus obtained, which is subsequently reacted with a dehydrating agent such as N-bromo-succinimide in dimethylformamide to form the corresponding compound of the formula III wherein R₂ has the meaning of R₂'. If it is intended to prepare a compound of the formula III wherein R₂ is halogen, a compound of the formula III wherein R₂ is hydrogen is halogenated, using conventional methods.

In this way, the following starting compounds of the formula III are obtained, for example:
3-Chloro-4,9-dihydro-10H-thieno[3,4-b][1,5]benzodiazepin-10-one,
4,9-Dihydro-3-methyl-10H-thieno[3,4-b][1,5]benzodiazepin-10-one,
m.p. 228°–230° C. (methanol),
4,9-Dihydro-1,3-dimethyl-10H-thieno[3,4-b][1,5]benzodiazepin-10-one, m.p. 195°–196° C., and
4,9-Dihydro-1-methyl-10H-thieno[3,4-b][1,5]benzodiazepin-10-one, m.p. 274°–276° C. (n-propanol).

The halocarbonic acid derivatives of the formula IV are known compounds.

The chlorocarbonic acid derivatives of the formula V and isocyanates of the formula Va are known compounds or can be obtained by methods described in the literature (cf., for example, I. W. Mathison et al., J.Pharm.Sci. 62, 158 [1963]; H. Hopff and H. Ohlinger, Angew. Chem. 61, 183 [1949]; W. Siefken, Liebigs Ann.Chem. 562, 75 [1949]; Houben-Weyl VIII, 117; Ullmann V, 72; L. C. Raiford and K. Alexander, J.Org.-Chem. 5, 306 [1940]; H. H. Saunders and R. J. Slocombe, Chem.Rev. 43, 203 [1948]; R. J. Slocombe, E. E. Hardy, J. H. Saunders and R. L. Jenkins, J.Amer.-Chem.Soc. 72, 1888 [1950]; H. Habad and A. G. Zeiler, Chem.Rev. 73, 75 [1973]).

The following examples illustrate the present invention and will enable others skilled in the art to understand it more completely. It should be understood, however, that the invention is not limited solely to the particular examples given below.

Preparation of Starting Compounds of Formula Ia

EXAMPLE 1

4-Chlorocarbonyl-4,9-dihydro-10H-thieno[3,4-b][1,5]benzodiazepin-10-one 16.2 gm (0.075 mol) of 4,9-dihydro-10H-thieno[3,4-b][1,5]benzodiazepin-10-one were admixed with 160 ml of diethylketone and 5.9 gm (0.075 mol) of pyridine at 40° C., and over a period of 20 minutes 75 ml of a 20% solution of phosgene (0.15 mol) in toluene were added thereto. The reaction mixture was stirred for 2 hours at 40° C. and then for 3 hours at 60° C. After cooling to room temperature, the mixture was stirred with 150 ml of water, then filtered, and the organic phase was separated, concentrated by evaporation in vacuo, and the residue was recrystallized from acetonitrile. 4-Chlorocarbonyl-4,9-dihydro-10H-thieno[3,4-b][1,5]benzodiazepin-10-one, m.p. of 244°–245° C. (decomp.), was obtained with a yield of 50% of theory.

In analogous manner:

(a) From 4,9-dihydro-10H-thieno[3,4-b][1,5]benzodiazepin-10-one and methyl chlorocarbonate in a mixture of dioxane and toluene, 4,9-dihydro-4-methoxycarbonyl-10H-thieno[3,4-b][1,5]benzodiazepin-10-one was obtained;

(b) From 4,9-dihydro-1-methyl-10H-thieno[3,4-b][1,5]benzodiazepin-10-one and phosgene in a mixture of dioxane and toluene, 4-chlorocarbonyl-4,9-dihydro-1-methyl-10H-thieno[3,4-b][1,5]benzodiazepin-10-one was obtained, m.p. 235°–236° C. (chloroform);

(c) From 4,9-dihydro-3-methyl-10H-thieno[3,4-b][1,5]benzodiazepin-10-one and phosgene in a mixture of dioxane and toluene, 4-chlorocarbonyl-4,9-dihydro-3-methyl-10H-thieno[3,4-b][1,5]benzodiazepin-10-one was obtained;

(d) From 4,9-dihydro-1,3-dimethyl-10H-thieno[3,4-b][1,5]benzodiazepin-10-one and phosgene in a dioxane toluene mixture, 4-chlorocarbonyl-4,9-dihydro-1,3-dimethyl-10H-thieno[3,4-b][1,5]benzodiazepin-10-one was obtained as an amorphous, foamy product which was further reacted without purification;

(e) From 3-chloro-4,9-dihydro-10H-thieno[3,4-b][1,5]benzodiazepin-10-one and phosgene in diethylketone, 3-chloro-4-chlorocarbonyl-4,9-dihydro-10H-thieno[3,4-b][1,5]benzodiazepin-10-one was obtained, m.p. 238°–240° C. (ethanol);

(f) From 4,9-dihydro-10H-thieno[3,4-b][1,5]benzodiazepin-10-one and benzyl chlorocarbonate in a dioxane toluene mixture, 4-benzyloxycarbonyl-4,9-dihydro-10H-thieno[3,4-b][1,5]benzodiazepin-10-one was obtained.

Preparation of End Product of Formula I

EXAMPLE 2

4,9-Dihydro-4-{[(1-methyl-4-piperidinyl)amino]carbonyl}-10H-thieno[3,4-b][1,5]benzodiazepin-10-one A suspension of 3.0 gm (0.0108 mol) of 4-chlorocarbonyl-4,9-dihydro-10H-thieno[3,4-b][1,5]benzodiazepin-10-one and 1.2 gm (0.0108 mol) of sodium carbonate in 100 ml of acetonitrile was refluxed, and then a solution of 1.2 gm (0.0108 mol) of 4-amino-1-methyl-piperidine in 10 ml of acetonitrile was added dropwise thereto. The mixture was refluxed for 2 hours, then suction-filtered while still hot, and the filtrate was concentrated by evaporation in vacuo. The residue was purified by column chromatography (silica gel, eluant: methylene chloride+cyclohexane+methanol+ammonia=102+23+23+3). The desired fraction was concentrated by evaporation in vacuo, and the residue was recrystallized from acetonitrile. Needles with an m.p. of 206°–208° C. The yield was 50% of theory.

In analogous manner:

(a) From 4-chlorocarbonyl-4,9-dihydro-10H-thieno[3,4-b][1,5]benzodiazepin-10-one and 1-methyl-4-methylaminopiperidine, 4,9-dihydro-4-{[N-methyl-N-(1-methyl-4-piperidinyl)amino]carbonyl}-10H-thieno[3,4-b][1,5]benzodiazepin-10-one was obtained.

(b) From 4,9-dihydro-4-chlorocarbonyl-10H-thieno[3,4-b][1,5]benzodiazepin-10-one and endo-3-amino-8-methyl-8-azabicyclo[3,2,1]octane, endo-4,9-dihydro-4-{[(8-methyl-8-azabicyclo[3,2,1]-oct-3-yl)amino]carbonyl}-10H-thieno[3,4-b][1,5]benzodiazepin-10-one was obtained, m.p. 203°–205° C. (acetonitrile);

(c) From 4-chlorocarbonyl-4,9-dihydro-1-methyl-10H-thieno[3,4-b][1,5]benzodiazepin-10-one and 4-amino-1-methylpiperidine, 4,9-dihydro-1-methyl-4-{[(1-methyl-4-piperidinyl)amino]carbonyl}-10H-thieno[3,4-b][1,5]benzodiazepin-10-one was obtained, m.p. 240.5°–241° C. (from ethyl acetate);

(d) From 4-chlorocarbonyl-4,9-dihydro-3-methyl-10H-thieno[3,4-b][1,5]benzodiazepin-10-one and 4-amino-1-methylpiperidine, 4,9-dihydro-3-methyl-4-{[(1-methyl-4-piperidinyl)amino]carbonyl}-10H-thieno[3,4-b][1,5]benzodiazepin-10-one was obtained;

(e) From 4-chlorocarbonyl-4,9-dihydro-1,3-dimethyl-10H-thieno[3,4-b][1,5]benzodiazepin-10-one and 4-amino-1-methyl-piperidine, 4,9-dihydro-1,3-dimethyl-4-{[(1-methyl-4-piperidinyl)amino]carbonyl}-10H-thieno[3,4-b][1,5]benzodiazepin-10-one was obtained, m.p. 136°–140° C. (acetonitrile);

(f) From 3-chloro-4-chlorocarbonyl-4,9-dihydro-10H-thieno[3,4][1,5]benzodiazepin-10-one and 4-amino-1-methylpiperidine, 3-chloro-4,9-dihydro-4-{[(1-methyl-4-piperidinyl)amino]carbonyl}-10H-thieno[3,4-b][1,5]benzodiazepin-10-one was obtained;

(g) From 4-chlorocarbonyl-4,9-dihydro-10H-thieno[3,4-b][1,5]benzodiazepin-10-one and endo-8-methyl-3-methylamino-8-azabicyclo[3,2,1]octane, endo-4,9-dihydro-4-{[N-methyl-N-(8-methyl-8-azabicyclo[3,2,1]oct-3-yl)amino]carbonyl}-10H-thieno[3,4-b][1,5]benzodiazepin-10-one was obtained, m.p. 259°–260° C. (ethanol);

(h) From 4-chlorocarbonyl-4,9-dihydro-10H-thieno[3,4-b][1,5]benzodiazepin-10-one and 1-amino-4-methyl-piperazine, 4,9-dihydro-4-{[(4-methyl-1-piperazinyl)amino]carbonyl}-10H-thieno[3,4-b][1,5-benzodiazepin-10-one was obtained, m.p. 240°–241° C. (2-propanol);

(i) From 4-chlorocarbonyl-4,9-dihydro-1-methyl-10H-thieno[3,4-b][1,5]benzodiazepin-10-one and 1-amino-4-methylpiperazine, 4,9-dihydro-1-methyl-4-{[(4-methyl-1-piperazinyl)amino]carbonyl}-10H-thieno[3,4-b][1,5]benzodiazepin-10-one was obtained;

(j) From 4-chlorocarbonyl-4,9-dihydro-3-methyl-10H-thieno[3,4-b][1,5]benzodiazepin-10-one and 1-amino-4-methylpiperazine, 4,9-dihydro-3-methyl-4-{[(4-methyl-1-piperazinyl)amino]carbonyl}-10H-thieno[3,4-b][1,5]benzodiazepin-10-one was obtained;

(k) From 4-chlorocarbonyl-4,9-dihydro-1,3-dimethyl-10H-thieno[3,4-b][1,5]benzodiazepin-10-one and 1-amino-4-methyl-piperazine, 4,9-dihydro-1,3-dimethyl-4-{[(4-methyl-1-piperazinyl)amino]carbonyl}-10H-thieno[3,4-b][1,5]benzodiazepin-10-one was obtained;

(l) From 3-chloro-4-chlorocarbonyl-4,9-dihydro-10H-thieno[3,4-b][1,5]benzodiazepin-10-one and 1-amino-4-methyl-piperazine, 3-chloro-4,9-dihydro-4-{[(4-methyl-1-piperazinyl)amino]carbonyl}-10H-thieno[3,4-b][1,5]benzodiazepin-10-one was obtained;

(m) From 4-chlorocarbonyl-4,9-dihydro-10H-thieno[3,4-b][1,5]benzodiazepin-10-one and exo-3-amino-8-methyl-8-azabicyclo[3,2,1]octane, exo-4,9-dihydro-4-{[(8-methyl-8-azabicyclo[3,2,1]-oct-3-yl)amino]carbonyl}-10H-thieno[3,4-b][1,5]benzodiazepin-10-one was obtained, m.p. 235°–237° C. (acetonitrile);

(n) From 4-chlorocarbonyl-4,9-dihydro-1-methyl-10H-thieno[3,4-b][1,5]benzodiazepin-10-one and endo-3-amino-8-methyl-8-azabicyclo[3,2,1]octane, endo-4,9-dihydro-1-methyl-4-{[(8-methyl-8-azabicyclo[3,2,1]oct-3-yl)amino]carbonyl}-10H-thieno[3,4-b][1,5]benzodiazepin-10-one was obtained;

(o) From 4-chlorocarbonyl-4,9-dihydro-3-methyl-10H-thieno[3,4-b][1,5]benzodiazepin-10-one and endo-3-amino-8-methyl-8-azabicyclo[3,2,1]octane, endo-4,9-dihydro-3-methyl-4-{[(8-methyl-8-azabicyclo[3,2,1]oct-3-yl)amino]carbonyl}-10H-thieno]3,4-b][1,5]benzodiazepin-10-one was obtained;

(p) From 4-chlorocarbonyl-4,9-dihydro-1,3-dimethyl-10H-thieno[3,4-b][1,5]benzodiazepin-10-one and endo-3-amino-8-methyl-8-azabicyclo[3,2,1]octane, endo-4,9-dihydro-1,3-dimethyl-4-{[(8-methyl-8-azabicyclo[3,2,1]oct-3-yl)amino]carbonyl}-10H-thieno[3,4-b][1,5]benzodiazepin-10-one was obtained;

(q) From 3-chloro-4-chlorocarbonyl-4,9-dihydro-10H-thieno[3,4-b][1,5]benzodiazepin-10-one and endo-3-amino-8-methyl-8-azabicyclo[3,2,1]octane, endo-3-chloro-4,9-dihydro-4-{[(8-methyl-8-azabicyclo[3,2,-1]oct-3-yl)amino]carbonyl}-10H-thieno[3,4-b][1,5]benzodiazepin-10-one was obtained, m.p. 158°–161° C. (acetonitrile);

(r) From 3-chloro-4-chlorocarbonyl-4,9-dihydro-10H-thieno[3,4-b][1,5]benzodiazepin-10-one and exo-3-amino-8-methyl-8-azabicyclo[3,2,1]octane, exo-3-chloro-4,9-dihydro-4-{[(8-methyl-8-azabicyclo[3,2,-1]oct-3-yl)amino]carbonyl}-10H-thieno[3,4-b][1,5]benzodiazepin-10-one was obtained, m.p. 224°–225° C. (from acetonitrile).

EXAMPLE 3

4,9-Dihydro-4-{[(1-methyl-4-piperidinyl)oxy]carbonyl}-10H-thieno[3,4-b][1,5]benzodiazepin-10-one was obtained from 4-chlorocarbonyl-4,9-dihydro-10H-thieno[3,4-b][1,5]benzodiazepin-10-one and 1-methyl-4-piperidinol, using the procedure described in Example 2. M.p. 189°–190° C. (from acetonitrile). Yield: 55% of theory.

The base thus obtained was dissolved in ethyl acetate, and a solution of hydrogen chloride in dioxane was added. The hydrochloride precipitated thereby was recrystallized from a mixture of ethanol and diethyl ether (1:1). M.p. 220°–222° C. (decomp.). In analogous manner:

(a) From 4-chlorocarbonyl-4,9-dihydro-1-methyl-10H-thieno[3,4-b][1,5]benzodiazepin-10-one and 1-methyl-4-piperidinol, 4,9-dihydro-1-methyl-4-{[(1-methyl-4-piperidinyl)oxy]carbonyl}-10H-thieno[3,4-b][1,5]benzodiazepin-10-one was obtained, m.p.201°–202° C. (ethyl acetate);

(b) From 4-chlorocarbonyl-4,9-dihydro-3-methyl-10H-thieno[3,4-b][1,5]benzodiazepin-10-one and 1-methyl-4-piperidinol, 4,9-dihydro-3-methyl-4-{[(1-methyl-4-piperidinyl)oxy]carbonyl}-10H-thieno[3,4-b][1,5]benzodiazepin-10-one was obtained;

(c) From 4-chlorocarbonyl-4,9-dihydro-1,3-dimethyl-10H-thieno[3,4-b][1,5]benzodiazepin-10-one and 1-methyl-4-piperidinol, 4,9-dihydro-1,3-methyl-4-{[(1-methyl-4-piperidinyl)oxy]carbonyl}-10H-thieno[3,4-b][1,5]benzodiazepin-10-one was obtained, m.p. 198°–200° C. (ethyl acetate);

(d) From 3-chloro-4-chlorocarbonyl-4,9-dihydro-10H-thieno[3,4-b][1,5]benzodiazepin-10-one and 1-methyl-4-piperidinol, 3-chloro-4,9-dihydro-4-{[(1-methyl-4-piperidinyl)oxy]carbonyl}-10H-thieno[3,4-b][1,5]benzodiazepin-10-one was obtained;

(e) From 4-chlorocarbonyl-4,9-dihydro-10H-thieno[3,4-b][1,5]benzodiazepin-10-one and 1-hydroxy-4-methylpiperazine, 4,9-dihydro-4-{[(4-methyl-1-piperazinyl)oxy]carbonyl}-10H-thieno[3,4-b][1,5]benzodiazepin-10-one was obtained;

(f) From 4-chlorocarbonyl-4,9-dihydro-1-methyl-10H-thieno[3,4-b][1,5]benzodiazepin-10-one and 1-hydroxy-4-methyl-piperazine, 4,9-dihydro-1-methyl-4-{[(4-methyl-1-piperazinyl)oxy]carbonyl}-10H-thieno[3,4-b][1,5]benzodiazepin-10-one was obtained;

(g) From 4-chlorocarbonyl-4,9-dihydro-10H-thieno[3,4-b][1,5]benzodiazepin-10-one and endo-8-methyl-8-azabicyclo[3,2,1]octan-3-ol, endo-4,9-dihydro-4-{[(8-methyl-8-azabicyclo[3,2,1]oct-3-yl)oxy]carbonyl}-10H-thieno[3,4-b][1,5]benzodiazepin-10-one was obtained;

(h) From 4-chlorocarbonyl-4,9-dihydro-1-methyl-10H-thieno[3,4-b][1,5]benzodiazepin-10-one and endo-8-methyl-8-azabicyclo[3,2,1]octan-3-ol, endo-4,9-dihydro-1-methyl-4-{[(8-methyl-8-azabicyclo[3,2,1]oct-3-yl)oxy]carbonyl}-10H-thieno]3,4-b][1,5-benzodiazepin-10-one was obtained;

(i) From 4-chlorocarbonyl-4,9-dihydro-3-methyl-10H-thieno[3,4-b][1,5]benzodiazepin-10-one and endo-8-methyl-8-azabicyclo[3,2,1]octan-3-ol, endo-4,9-dihydro-3-methyl-4-{[(8-methyl-8-azabicyclo[3,2,1]oct-3-yl)oxy]carbonyl}-10H-thieno[3,4-b][1,5-benzodiazepin-10-one was obtained;

(j) From 4-chlorocarbonyl-4,9-dihydro-1,3-dimethyl-10H-thieno[3,4-b][1,5]benzodiazepin-10-one and endo-8-methyl-8-azabicyclo[3,2,1]octan-3-ol, endo-4,9-dihydro-1,3-dimethyl-4-{[(8-methyl-8-azabicyclo[3,2,1]oct-3-yl)oxy]carbonyl}-10H-thieno[3,4-b][1,5]benzodiazepin-10-one was obtained;

(k) From 3-chloro-4-chlorocarbonyl-4,9-dihydro-10H-thieno[3,4-b][1,5]benzodiazepin-10-one and endo-8-methyl-8-azabicyclo[3,2,1]octan-3-ol, endo-3-chloro-4,9-dihydro-4-{[(8-methyl-8-azabicyclo[3,2,1]oct-3-yl)oxy]carbonyl}-10H-thieno[3,4-b][1,5]benzodiazepin-10-one was obtained;

(l) From 4-chlorocarbonyl-4,9-dihydro-10H-thieno[3,4-b][1,5]benzodiazepin-10-one and exo-8-methyl-8-azabicyclo[3,2,1]octan-3-ol, exo-4,9-dihydro-4-{[(8-methyl-8-azabicyclo[3,2,1]oct-3-yl)oxy]carbonyl}-10H-thieno[3,4-b][1,5]benzodiazepin-10-one was obtained.

The novel thienobenzodiazepinones of the formula I and their non-toxic, pharmacologically acceptable acid addition salts have useful pharmacodynamic properties. More particularly, they exhibit anti-ulcerogenic activity, inhibit gastric acid secretion, and have favorable effects on various disorders of the gastro-intestinal tract, especially irritable colon, in warm-blooded animals.

The above pharmacodynamic properties of the compounds of the formula I and their non-toxic acid addition salts were ascertained by the standard test methods described below.

A favorable relation between anti-ulcerogenic and anti-secretory effects, on the one hand, and the undesirable effects on pupil size and the secretion of tears and saliva, on the other hand, which occurs particularly with therapeutic agents having an anti-cholinergic component, is of particular importance in the therapeutic use of the substances. The following tests show that the compounds of the formula I according to the invention have surprisingly favorable characteristics in this respect.

Investigation of the Selectivity of the Antimuscarinic Activity

Object

Oxotremorine, a specific agonist for muscarinic receptors, produces lesions in the mucous membrane of the stomach in rats and increases their secretion of saliva. This test method was chosen so that any selective activity of an antimuscarinic substance on the stomach could be identified.

Method

Ten female albino rats (of the Crl:COBS-CD (SD) BR strain) with a body weight of from 120 to 150 gm were used in each treatment group and were kept without food for 24 hours before the start of the test, but given free access to drinking water.

In order to determine, in preliminary tests, the muscarinic effect of oxotremorine on each of the symptoms studied, a dosage/activity curve was drawn up with at least three dosages for each symptom.

When testing the antimuscarinic substances, the dosage of oxotremorine which triggered the symptom in question in 90 to 100% of the animals in the preliminary tests was used.

Lesion in mucous membrane of stomach: 0.62 mg/kg i.v.

Secretion of saliva: 0.083 mg/kg i.v.

Each antimuscarinic substance was administered intravenously in uniformly graduated doses 15 minutes before the oxotremorine was administered. Control groups were given corresponding quantities of the solvent and suspending agent instead of the test substance.

Immediately after the oxotremorine was administered, the animals were placed in a glass cage for 15 minutes and observed.

The test for the effect on the oxotremorine-induced secretion of saliva was carried out as a blind test, i.e. the tester did not know which treatment the animals had been given.

The results were expressed as the percentage inhibition of the oxotremorine effect (the percentage of animals which did not show the symptom in question). The $ED_{50}$ values were determined using the method described by LITCHFIELD and WILCOXON [J. Pharmacol. Exp.Ther. 96, 99, (1949)].

The effects on lesions of the mucous membrane of the stomach were evaluated as follows:

The lesions of the gastric mucous membrane were produced by intravenous injection of 0.62 mg/kg of oxotremorin 30 minutes after the oral administration of 1 mg/kg of neostigmine (a cholinesterase inhibitor). 60 minutes after the administration of the neostigmine, the animals were killed, the stomachs were removed, opened and examined for the presence of any lesions in the mucous membrane. The protective effect of the test substances was expressed as the percentage inhibition (percentage of animals without lesions). The $ED_{50}$ and $ED_{70}$ values were determined using the method of LITCHFIELD and WILCOXON (supra).

Mydriasis

The effect of the test substances on the pupil size in rats was investigated as follows:

The substances were administered intravenously to groups of 10 animals in at least three uniformly graduated doses. The pupil size was then observed for 10 minutes to see if there were any changes (mydriasis or miosis), and again the test was carried out blind, i.e. the tester did not know what preliminary treatment the animals had received. The percentage of test animals in which mydriasis occurred was determined. The $ED_{50}$ values were again determined using the method of LITCHFIELD and WILCOXON (supra).

2. Studies of Binding to Muscarinic Receptors: Determination of the $IC_{50}$ value The organ donors were male Sprague-Dawley rats with a body weight of from 180 to 220 gm. After the heart, stomach and cerebral cortex had been removed, the remainder of the operation was carried out in ice-cold Hepes-HCl buffer (pH 7.4; 100 m molar NaCl, 10 m molar $MgCl_2$). The smooth muscle of the fundus of the stomach was separated from the mucous membrane of the stomach and subjected to preliminary homogenization. The whole heart was cut up with scissors. All the organs were then homogenized in a Potter apparatus.

For the binding test, the homogenized organs were diluted as follows:

Smooth muscle of the fundus of the stomach—1: 100
Whole heart—1: 250
Cerebral cortex—1:3000

The homogenized organ preparations were incubated at a specific concentration of the radioligand and with a series of concentrations of the non-radioactive test substances in an Eppendorf centrifuge tube at 30° C. The duration of incubation was 45 minutes. 0.3 n molar $^3$H-N-methylscopolamine ($^3$H-NMS) was used as the radioligand. After incubation had been brought to an end by centrifuging at 14,000 g, the radioactivity in the pellet was determined. It represents the sum of the specific and non-specific binding of $^3$H-NMS. The proportion of non-specific binding was defined as the radioactivity which was bound in the presence of 1$\mu$ molar quinuclidinyl benzylate. Four measurements were taken in each case. The $IC_{50}$ values of the nonlabelled test substances were determined graphically. They represent the concentration of test substance at which the specific binding of $^3$H-NMS to the muscarinic receptors in the various organs was inhibited by 50%.

The following table shows the results of these tests for a few representative species of the genus represented by formula I, where A = 4,9-Dihydro-4-{[(1-methyl-4-piperidinyl)oxy]carbonyl}-10H-thieno[3,4-b][1,5]benzodiazepin-10-one, B = 4,9-Dihydro-4-{[(1-methyl-4-piperidinyl)amino]carbonyl}-10H-thieno[3,4-b][1,5]benzodiazepin-10-one, and C = 4,9-Dihydro-4-{[(4-methyl-1-piperazinyl)amino]carbonyl}-10H-thieno[3,4-b][1,5]benzodiazepin-10-one.

| Compound | Receptor binding tests $IC_{50}$ [n mol $l^{-1}$] | | | Oxotremorine test [μg/kg] i.v. | | | Mydriasis $ED_{50}$ [μg/kg] i.v. |
| --- | --- | --- | --- | --- | --- | --- | --- |
| | Cortex | Smooth muscle fundus of stomach | Heart | Anti-ulcerogenic effect $ED_{50}$ | $ED_{70}$ | Inhibition of salivation $ED_{50}$ | |
| A | 40 | 200 | 180 | 17 | 25 | 100 | 110 |
| B | 30 | 300 | 220 | 17 | 44 | 40 | 37 |
| C | 20 | 200 | 90 | | 19 | | 30 |

The results in the above table show that the compounds in question generally have a high affinity for muscarinic receptors. Moreover, the results show that the new compounds of the formula I differentiate between muscarinic receptors in different types of tissue. This is clear from the considerably lower $IC_{50}$ values in the tests on preparations from the cerebral cortex compared with those of the smooth muscle of the stomach and heart.

The pharmacological data in the above table show - in complete agreement with the receptor binding studies - that the formation of oxotremorine-induced lesions in the mucous membrane of the stomach is inhibited by the abovementioned compounds, even at doses at which no diminution of salivation and no mydriasis can be observed.

Thus, the substituted thienobenzodiazepinones of the formula I and non-toxic acid addition salts thereof have useful properties which make them commercially viable, and are characterized in particular by an excellent protective effect on the stomach and intestines in warm-blooded animals; for example, they inhibit the formation of gastric ulcers. Moreover, they have a useful therapeutic range, thanks to their low toxicity and the absence of any significant side effects.

The excellent activity of the substituted thienobenzodiazepinones of the formula I and their non-toxic pharmacologically acceptable acid addition salts makes it possible to use them in both human and veterinary medicine for the treatment and prophylaxis of diseases due to disorders of the stomach or intestines. They may be used, for example, to treat acute and chronic gastric and duodenal ulcers, gastritis and gastric hyperacidity in humans and animals.

For pharmaceutical purposes the compounds of the formula I or their non-toxic, pharmacologically acceptable acid addition salts are administered to warm-blooded animals perorally, parenterally or rectally as active ingredients in customary pharmaceutical compositions, that is, compositions consisting essentially of an inert pharmaceutical carrier and an effective amount of the active ingredient, such as tablets, coated pills, capsules, wafers, powders, solutions, suspensions, emulsions, syrups, suppositories, tea-making compositions and the like. The daily dose for oral administration is generally between 0.01 and 5, preferably between 0.02 and 2.5, more particularly between 0.05 and 1.0 mg/kg body weight, generally administered in the form of several, preferably from 1 to 3, individual doses to achieve the desired results.

If the substituted thienobenzodiazepinones of the formula I and/or non-toxic, pharmacologically acceptable acid addition salts thereof are to be used to treat the diseases mentioned above, the pharmaceutical preparations may also contain one or more pharmacologically active components from other groups of medicaments, such as antacids, for example aluminum hydroxide or magnesium aluminate; secretion-inhibitors such as $H_2$-blockers, for example cimetidine or ranitidine; gastric and intestinal therapeutic agents, such as metoclopramide, bromoprid and tiaprid; tranquilizers such as benzodiazepines, for example diazepam and oxazepam; spasmolytics such as bietamiverine, camylofine; anticholinergics such as oxyphencyclimine and phencarbamide; glucocorticoids such as prednisolone, fluocortolone and bethamethasone; non-steroidal antiphlogistic agents such as arylacetic acids and arylpropionic acids, heteroarylacetic acids and heteroarylpropionic acids, benzothiazine carboxamide dioxides, pyrazolidinediones or quinazolinones, for instance Ibuprofen, naproxen, dichlofenac, fenbufen, flurbiprofen, indomethacin, lonazolac, sudoxicam, piroxicam, phenylbutazone, bumadizon-calcium or proquazone; local anesthetics such as tetracaine and procaine; and optionally also enzymes; vitamins, amino acids, etc.

The following examples illustrate a few pharmaceutical compositions comprising a compound of the formula I as an active ingredient and represent the best modes contemplated of using the invention. The parts are parts by weight unless otherwise specified.

EXAMPLE 4

Tablets

The tablet composition is compounded from the following ingredients:

| | |
| --- | --- |
| 4,9-Dihydro-4-{[(1-methyl-4-piperidinyl)-oxy]carbonyl}-10H—thieno[3,4-b][1,5]-benzodiazepin-10-one hydrochloride | 5.0 parts |
| Lactose | 148.0 parts |
| Potato starch | 65.0 parts |
| Magnesium stearate | 2.0 parts |
| | 220.0 parts |

Preparation

A 10% slurry is prepared from part of the potato starch by heating. The active ingredient, lactose and remaining potato starch are mixed together and granulated with the slurry through a screen with a mesh size of 1.5 mm. The granulate is dried at 45° C., passed through the screen again, mixed with magnesium stearate and compressed to form 220 mg-tablets, each of which contains 5 mg of the active ingredient.

EXAMPLE 5

Coated Tablets

The tablets prepared according to Example 4 are coated in conventional manner with a thin shell consisting essentially of a mixture of sugar and talcum. The finished coated tablets are polished with beeswax. Weight of coated tablet: 300 mg

EXAMPLE 6

Injection Solution

The solution is compounded from the following ingredients:

| | |
|---|---|
| 4,9-Dihydro-4-{[(1-methyl-4-piperidinyl)-oxy]carbonyl}-10H—thieno[3,4-b][1,5]-benzodiazepin-10-one hydrochloride | 1.0 parts |
| Sodium chloride | 8.0 parts |
| Distilled water    q.s. ad | 1000.0 parts by vol. |

Preparation

The active ingredient and the sodium chloride are dissolved in a sufficient amount of distilled water, and the solution is diluted with additional distilled water to the indicated volume and then filtered until free from suspended particles. The filtrate is filled into 1 cc-ampules which are then sealed and sterilized for 20 minutes at 120° C. The contents of each ampule are an injectable solution containing 1 mg of the active ingredient.

EXAMPLE 7

Suppositories

The suppository composition is compounded from the following ingredients:

| | |
|---|---|
| 4,9-Dihydro-4-{[(1-methyl-4-piperidinyl)-oxy]carbonyl}-10H—thieno[3,4-b][1,5]-benzodiazepin-10-one hydrochloride | 5.0 parts |
| Suppository base (e.g. cocoa butter) | 1,695.0 parts |
| | 1,700.0 parts |

Preparation

The finely powdered active ingredient is homogeneously blended into the molten suppository base which has been cooled to 40° C. 1700 mg-portions of the composition are poured at 37° C. into slightly chilled suppository molds and allowed to harden therein. Each suppository contains 5 mg of the active ingredient.

EXAMPLE 8

Drop Solution

The solution is compounded from the following ingredients:

| | |
|---|---|
| 4,9-Dihydro-4-{[(1-methyl-4-piperidinyl)-oxy]carbonyl}-10H—thieno[3,4-b][1,5]-benzodiazepin-10-one hydrochloride | 0.5 parts |
| Methyl p-hydroxybenzoate | 0.035 parts |
| Propyl p-hydroxybenzoate | 0.015 parts |
| Anise oil | 0.05 parts |
| Menthol | 0.06 parts |
| Pure ethanol | 10.0 parts |
| Sodium cyclamate | 1.0 parts |
| Glycerol | 15.0 parts |
| Distilled water | 100.0 parts by vol. |

Preparation

The active ingredient and sodium cyclamate are dissolved in about 70 parts of distilled water and glycerol is adddd thereto. The p-hydroxybenzoates, anise oil and menthol are dissolved in the ethanol, and this solution is added to the aqueous solution while stirring. Finally, the mixture is made up to 100 parts by volume with water and filtered to remove any suspended particles. The filtrate is filled into 100 cc-bottles equipped with a dropping spout. 1 ml (about 20 drops) of the solution contains 5 mg of the active ingredient.

Any one of the other compounds embraced by formula I or a non-toxic, pharmacologically acceptable acid addition salt thereof may be substituted for the particular active ingredient in Examples 4 through 8. Likewise, the amount of active ingredient in these illustrative examples may be varied to achieve the dosage unit range set forth above, and the amounts and nature of the inert pharmaceutical carrier ingredients may be varied to meet particular requirements.

While the present invention has been illustrated with the aid of certain specific embodiments thereof, it will be readily apparent to others skilled in the art that the invention is not limited to these particular embodiments, and that various changes and modifications may be made without departing from the spirit of the invention or the scope of the appended claims.

We claim:

1. A compound of the formula

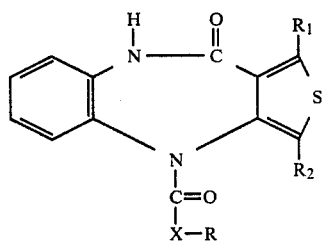

wherein

R is 1-methyl-4-piperidinyl, 4-methyl-1-piperazinyl, or 3α- or 3β-tropanyl, each of which may optionally have another methyl substituent attached to the heterocyclic ring;

$R_1$ is hydrogen or alkyl of 1 to 4 carbon atoms;

$R_2$ is hydrogen, halogen or alkyl of 1 to 4 carbon atoms; and

X is oxygen, —NH— or —N(CH$_3$)—; a geometric isomer or enantiomer thereof; or a non-toxic, pharmacologically acceptable acid addition salt thereof.

2. A compound of claim 1, wherein

R is 1-methyl-4-piperidinyl, 4-methyl-1-piperazinyl, or endo- or exo-8-methyl-8-azabicyclo[3,2,1]-oct-3-yl;

$R_1$ is hydrogen or methyl;

$R_2$ is chlorine, hydrogen or methyl; and

X is oxygen, —NH— or —N(CH$_3$)—; a geometric isomer or enantiomer thereof; or a non-toxic, pharmacologically acceptable acid addition salt thereof.

3. A compound of claim 1, which is 4,9-dihydro-4-{[(1-methyl-4-piperidinyl)oxy]carbonyl}-10H-thieno[3,4-b][1,5]benzodiazepin-10-one or a non-toxic, pharmacologically acceptable acid addition salt thereof.

4. A compound of claim 1, which is 4,9-dihydro-4-{[(1-methyl-4-piperidinyl)amino]carbonyl}-10H-thieno[3,4-b][1,5]benzodiazepin-10-one or a non-toxic, pharmacologically acceptable acid addition salt thereof.

5. A compound of claim 1, which is 4,9-dihydro-4-{[(4-methyl-1-piperazinyl)amino]carbonyl}-10H-thieno[3,4-b][1,5]benzodiazepin-10-one or a non-toxic, pharmacologically acceptable acid addition salt thereof.

6. A compound of the formula

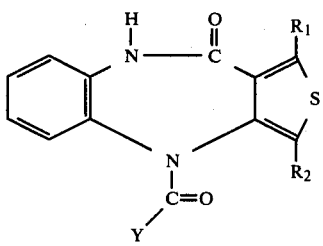

wherein

R₁ and R₂ have the same meanings as in claim 1;

Y is halogen or —OR₃; and

R₃ is unsubstituted or halo-substituted alkyl of 1 to 5 carbon atoms, phenyl, halo-substituted phenyl, nitro-substituted phenyl, or aralkyl of 7 to 15 carbon atoms.

7. An anti-ulcerogenic pharmaceutical composition consisting essentially of an inert pharmaceutical carrier and an effective anti-ulcerogenic amount of a compound of claim 1.

8. The method of inhibiting the formation of gastric ulcers in a warm-blooded animal in need thereof, which comprises perorally, parenterally or rectally administering to said animal an effective anti-ulcerogenic amount of a compound of claim 1.

* * * * *

UNITED STATES PATENT AND TRADEMARK OFFICE
CERTIFICATE OF CORRECTION

PATENT NO. : 4,410,527

DATED : October 18, 1983

INVENTOR(S) : WOLFHARD ENGEL ET AL.

It is certified that error appears in the above-identified patent and that said Letters Patent is hereby corrected as shown below:

Column 12, line 17: "]3,4-b]" should be -- [3,4-b] --.

Column 16, line 25: "1buprofen" should be -- libuprofen --.

line 26: "dichlofenac" should be -- diclofenac --.

Signed and Sealed this

*Twenty-first* Day of *August 1984*

[SEAL]

*Attest:*

GERALD J. MOSSINGHOFF

*Attesting Officer*     *Commissioner of Patents and Trademarks*